United States Patent [19]
Bougamont et al.

[11] Patent Number: 5,239,992
[45] Date of Patent: Aug. 31, 1993

[54] LOOSE POWDER INHALER WITH INHALATION-ACTUATED DOSING PISTON

[75] Inventors: Jean-Louis Bougamont; Alain Behar, both of Eu, France

[73] Assignee: Societe Francaise d'Aerosols et de Bouchage, Le Treport, France

[21] Appl. No.: 891,626

[22] Filed: Jun. 1, 1992

[30] Foreign Application Priority Data

May 30, 1991 [FR] France ............... 91 06531

[51] Int. Cl.$^5$ ................. A61M 15/00; A61M 16/00; B05D 7/14; B65D 83/06
[52] U.S. Cl. .................. 128/203.15; 128/203.13
[58] Field of Search ............. 128/203.12–203.15, 128/203.18–203.24, 200.24

[56] References Cited

U.S. PATENT DOCUMENTS

| | | | |
|---|---|---|---|
| 2,587,215 | 2/1952 | Priestly | 128/203.15 |
| 3,257,961 | 6/1966 | Schlenker . | |
| 4,446,862 | 5/1984 | Baum et al. | 128/203.15 |
| 4,524,769 | 6/1985 | Wetterlin | 128/203.15 |
| 5,113,855 | 5/1992 | Newhouse | 128/203.12 |
| 5,161,524 | 11/1992 | Evans | 128/203.12 |
| 5,176,132 | 1/1993 | Drought et al. | 128/203.15 |

FOREIGN PATENT DOCUMENTS

| | | | |
|---|---|---|---|
| 2233236A1 | 9/1991 | United Kingdom | 128/200.23 |
| WO90/13327 | 11/1990 | World Int. Prop. O. | 128/203.15 |
| WO90/13328 | 11/1990 | World Int. Prop. O. | 128/203.15 |

Primary Examiner—Edgar S. Burr
Assistant Examiner—Kimberly L. Asher
Attorney, Agent, or Firm—Pennie & Edmonds

[57] ABSTRACT

An inhaler for powder products comprising a housing having an oral suction mouthpiece, a piston contained within the housing for movement in opposite directions, and an elastic member for urging the piston in one direction. The mouthpiece connects with a chamber in which the piston is located so that inhaling through the mouthpiece draws the piston toward the user's mouth. The piston includes a charging cavity for holding a charge of powder product. The cavity communicates with the internal volume of the mouthpiece as the piston is drawn toward the user's mouth whereby the charge is dispensed and inhaled by the user.

9 Claims, 4 Drawing Sheets

LOOSE POWDER INHALER WITH INHALATION-ACTUATED DOSING PISTON

BACKGROUND OF THE INVENTION

A certain number of medicaments formulated in powder form are orally inhaled by way of an inhaler having a mouthpiece for insertion into the user's mouth. These are in particular medicaments for asthma and other pulmonary diseases. A difficulty is that sometimes the patient has problems in synchronizing his inhalation with the manual operation of the distributor part of the inhaler so that inhalation occurs at the time when the powder is expelled from its source (which is sometimes done in an eddy current) and fed to the mouthpiece for inhaling.

SUMMARY OF THE PRESENT INVENTION

The object of the invention is to supply an inhaler able to ensure both a correct charge of the powder, i.e., the active agent, and a good utilization of the charge by a maximum precisely timed inhalation in the direction of the respiratory tract. More specifically, the inhaler essentially comprises a housing having an oral inhalation mouthpiece associated with a piston which is movable in an air chamber under two opposing actions, one being the retraction action of an elastic means and the other the attracting action of the pressure drop caused by an inhalation, on the part of the patient or user, through the mouthpiece.

The piston carries at least one transfer or charging cavity. This cavity is directly linked or in communication with a product reserve chamber fitted to the housing, when the piston is moved to one end of its movement under the influence of the elastic means. At the other end of the piston's movement, the cavity is linked by an adequate channel to the mouthpiece of the inhaler. Preferably, the communications of the cavity open slightly before the end of each of the successive movements of the piston.

According to an advantageous feature, the piston also closes one side of a secondary air chamber, and upon its retraction places this chamber under vacuum; and at the end of the retraction travel, the charging cavity links the reserve chamber with the vacuumizing chamber, so as to create therein a brief suction which will improve the filling of the charge cavity, if the powder has an imperfect outflow.

Moreover, appropriately constricted passages can link both air chambers with the exterior of the housing, more particularly through the mouthpiece, so as to partly dampen their internal pressure variations. Advantageously, suction on the passage to the secondary chamber is only allowed in a single direction by a valve, slide valve or sleeve controlled with clearance by the piston. The possible construction types for such a mechanism are well known to those making various miniaturized pumps. To provide the passages in the most advantageous manner, the housing is in the form of an injection molded box or case containing the piston, its auxiliary members and, if need be, the product reserve.

The inhaler permits an effective inhalation of a powder medicament by making the distribution of each charge of powder dependent on the inhalation movement of the patient.

A more detailed description is given hereinafter relative to an embodiment and the attached drawings, so as to permit a better understanding of the apparatus and its operation. The expert in connection with pumps and distributors will be able to find numerous constructional variants to said structure, with respect to the arrangement of the members and in particular the construction of the valve or the various channels, obtained by the association of openings or grooves made on the various parts and intended more particularly to avoid moulding problems.

DESCRIPTION OF THE PREFERRED EMBODIMENTS

Figure 1:
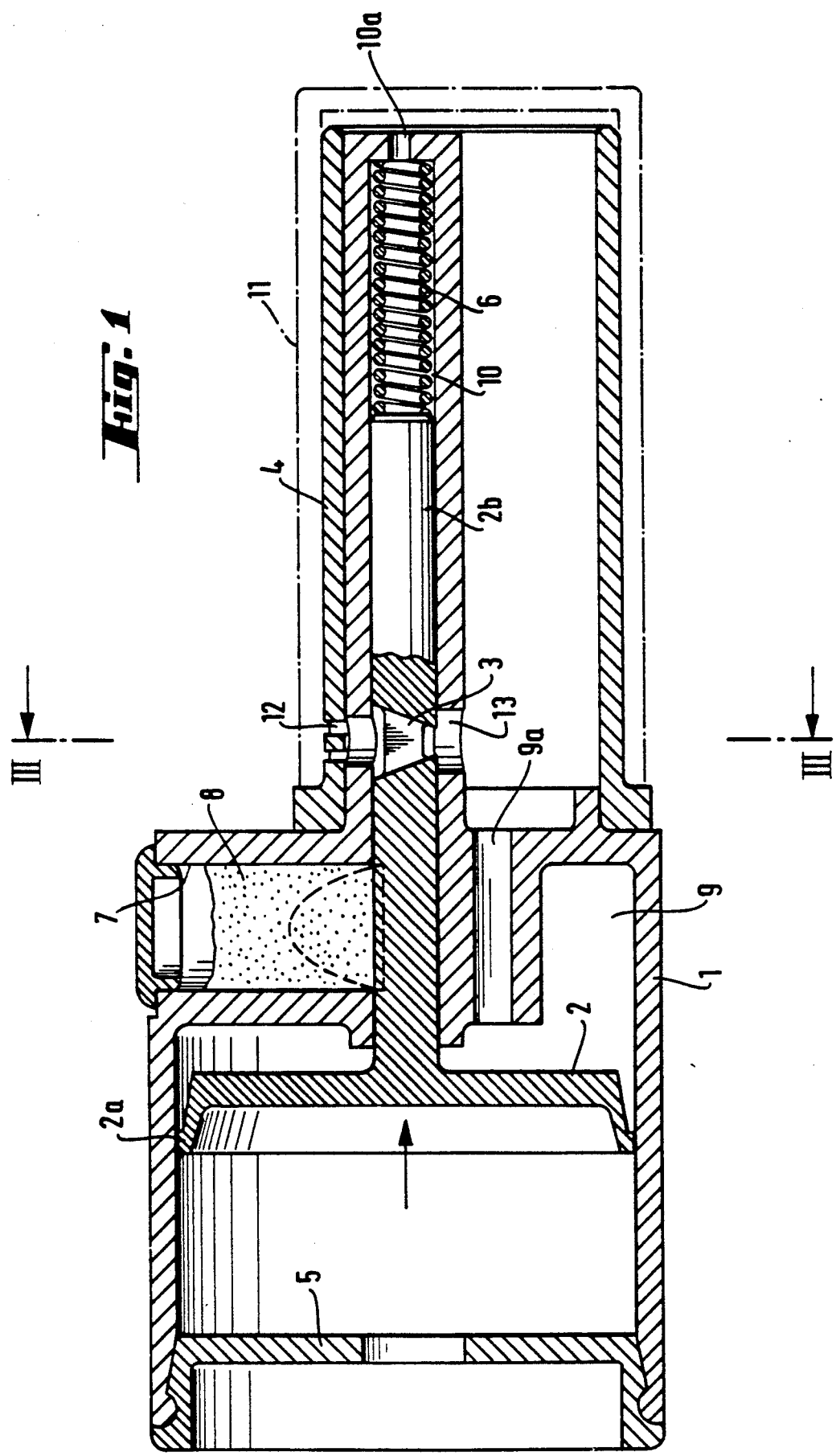
FIG. 1 is an elementary embodiment of the apparatus shown in cross-section.
Figure 2:
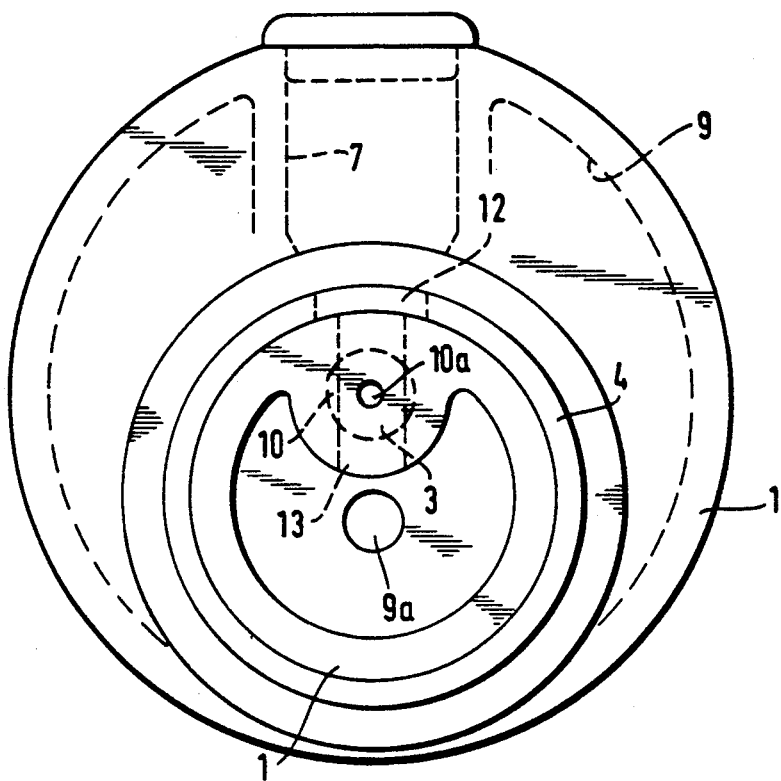
FIG. 2 is an end view of the embodiment shown in FIG. 1.

The inhaler includes a housing 1 in which is placed a piston means 2 having a significant cross-section on either the piston head or piston end parts, 2a, 2b, respectively. The piston means is also provided with a single or multiple recess forming a charge cavity 3, whose volume corresponds to the desired medicament dose or charge to be dispensed and inhaled.

The housing 1 carries a mouthpiece at one end of the housing. The mouthpiece is defined by an oral tip or end fitting 4. A ring or abutment diaphragm 5, which is open to the air, encloses the piston 2, at the other end of the housing. The piston can move to a first position, the final extent of which is against the diaphragm 5. In the first position, the cavity 3 is placed facing a hollow shaft part 7 of the housing. This hollow shaft contains the powder medicament reserve 8. The construction of the inhaler is such that the reserve 8 is placed on the top and the powder drops by gravity into and fills the charge cavity 3.

The piston means 2 of the inhaler is disposed in and slides in a chamber in the housing. In the embodiment of FIG. 1 the piston head 2a slides in a main air chamber 9 and its lip forms a seal against the chamber wall. FIG. 1 shows the piston at the end of the inhalation phase. A further or secondary air chamber 10 is provided in the housing for the piston rod part 2b of the piston means. As evident from FIG. 1, the piston rod part 2b is slidable in this chamber 10. An elastic means in the form of a spring 6, located in the chamber 10, acts on the said rod to urge the piston means to its first position with the charge cavity 3 aligned with the reserve 8. However, it is clear that different arrangements could be adopted and in particular the reserve 8 could be axially located in the housing or the spring could be placed in the chamber 9 and not in the chamber 10.

In the same way, the cross-sections of the various members are shown circular throughout without any predetermination of proportions, whereas in reality they will be adapted to the existence of a base and finger impressions facilitating and orienting the connection of the apparatus, and dependent on the shape of the mouth, the outflow of powder, etc. The cross-sectional size of the chambers 9 and 10, for example, can be reversed so that during the inhalation phase, the piston rod 2a would provide the primary surface against which the negative pressure would operate to draw the piston means toward the user's mouth.

In the embodiment of FIG. 1, a connecting orifice 9a links the main air chamber 9 with the mouthpiece. If the patient, who has previously removed the protective cap 11, places the oral end fitting of the mouthpiece 4 in his mouth and inhales, the orifice 9a transmits to the chamber 9 the vacuum caused by the inhalation and the piston means 2 is drawn toward the user's mouth, while compressing the spring 6. In the same way, an orifice 10a can vent the secondary air chamber 10 of both embodiments of FIGS. 1 and 4, and preferably, as shown in FIG. 1 of the drawings, this chamber can be connected to the internal space of the mouthpiece, so as to ensure that the inhalatory effort of the patient is transmitted to the entire cross-section of the piston means, that is, to both the piston head 2a and piston rod 2b. At least one of the orifices can also be calibrated so as to dampen the displacements of the piston means. More particularly, the orifice 10a of the secondary chamber 10 can be calibrated, the latter then serving as a brake, as well as a motor. The orifice 10a must be relatively narrow. It could even be closed completely by a valve and then the rebalancing of the pressure in the inoperative state would occur more slowly as a result of the action of the sealing imperfections.

Figure 3:
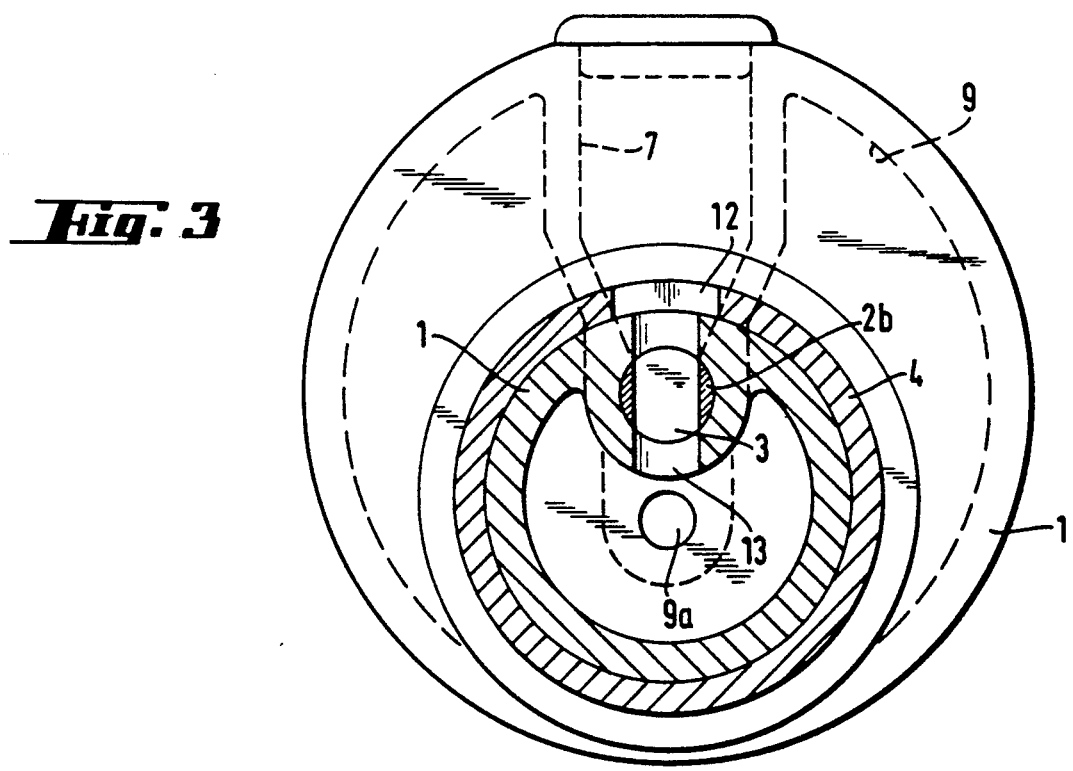
FIG. 3 is a section along III—III of FIG. 1.

In the final part of the travel of the piston means toward the user's mouth, in the manner shown in FIGS. 1 and 3, the cavity 3 is positioned in communication with both an air inlet vent 12 and an opposite dispensing passage 13 linking it with the interior volume of the end fitting of the mouthpiece. This internal space is vented with an adequate pressure drop; and, with the inhalation of the patient continuing, the thus formed air flow through the vent 12, charge cavity 3 and passage 13 moves the powder charge into the end fitting where it is stirred up in the internal volume of the mouthpiece and then moved towards the patient's mouth, where it is inhaled. By acting on the shape of the successive passages, it is possible to obtain a more or less durable entrainment during the movement of the cavity 3 in communication with the vent 12 and passage 13.

As soon a aspiration ends, the spring 6 returns the piston means into the first position, which enables a new powder dose or charge to enter the cavity 3, aided by the slight return abutment impact. The spring 6 must have an adequate force to be able to move the piston, but must not be too powerful for the forces of the patient, i.e., the piston means must have an adequate effective cross-section in the surfaces of the piston head or rod or both to overcome the force of the spring upon inhaling of the user.

Figure 4:
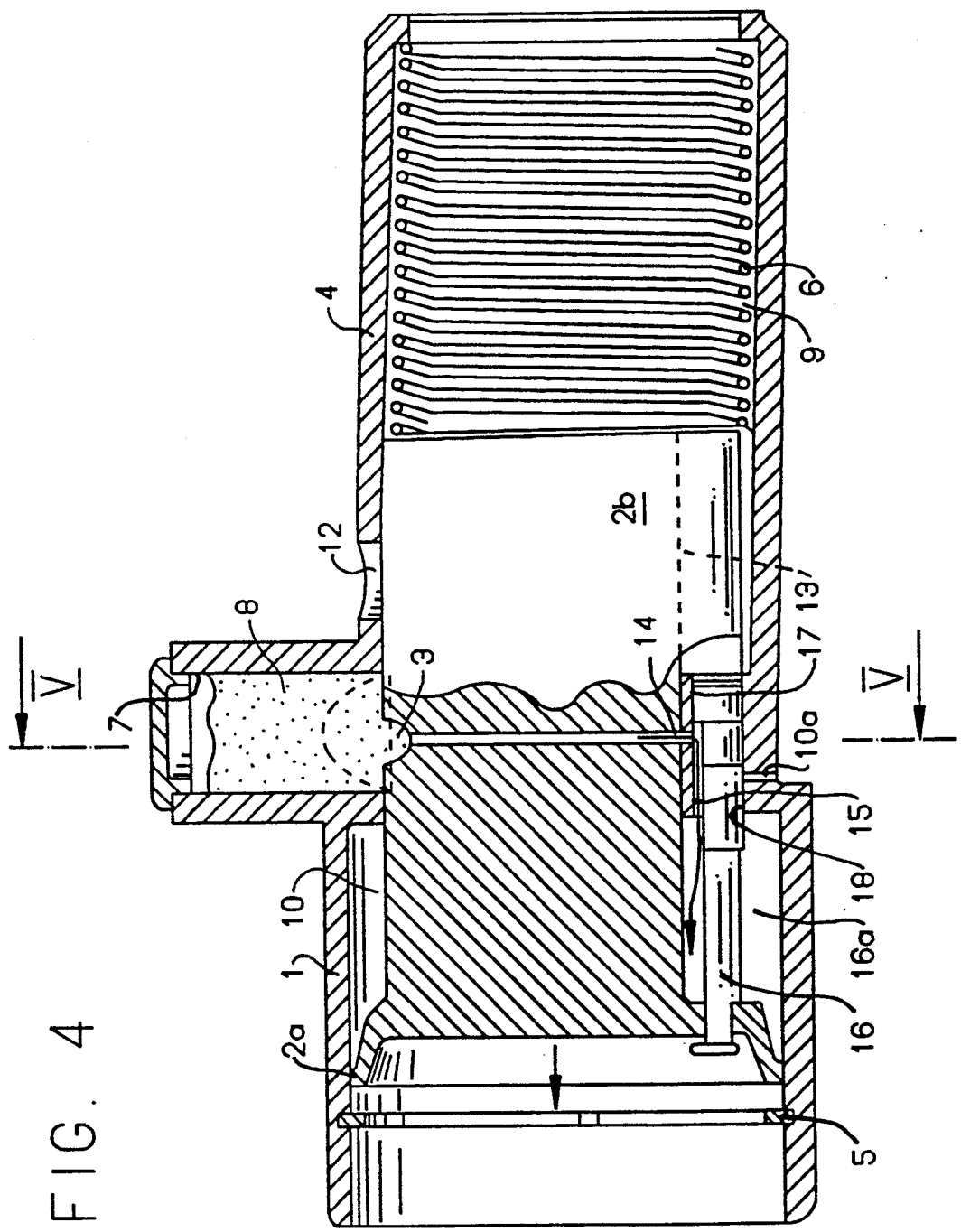
FIG. 4 is a view similar to FIG. 1 of another embodiment using suction feeding of the product charge.

FIG. 4 relates to a variant for improving the initial filling with powder of the charge cavity 3. It essentially consists of adding a narrow channel which communicates with the charge cavity 3 when the piston means 2 arrives in the vicinity of its first position in order to connect the cavity to the secondary chamber 10. It is clear that the displacement of the piston to the left of the drawing during its retraction to its first position can then have a brief suction effect on the powder aiding the dropping of the latter into the cavity 3.

In the embodiment of FIG. 4, the chamber 10 is shown at the left of the inhaler and the channel mentioned above is shown at 14 as communicating with the chamber 10 through a bore 15 in the housing. The suction effect is essentially dependent on the value of the pressure reduction in the chamber 10 as produced by the force of the spring 6 and this value increases with the decrease in the cross-section of the chamber compared with the total effective cross-section of the piston.

To avoid the creation of a harmful back-pressure in the advance phase of the piston means toward the user's mouth and during the taking of the medicament, it is then particularly useful to give the piston head 2a the shape of a flexible rearwardly turned lip at its outer periphery. This enables it to function as a channel to let air escape from the chamber 9 during the advance phase of the piston operation and thus to also serve as a delivery valve.

Figure 5:
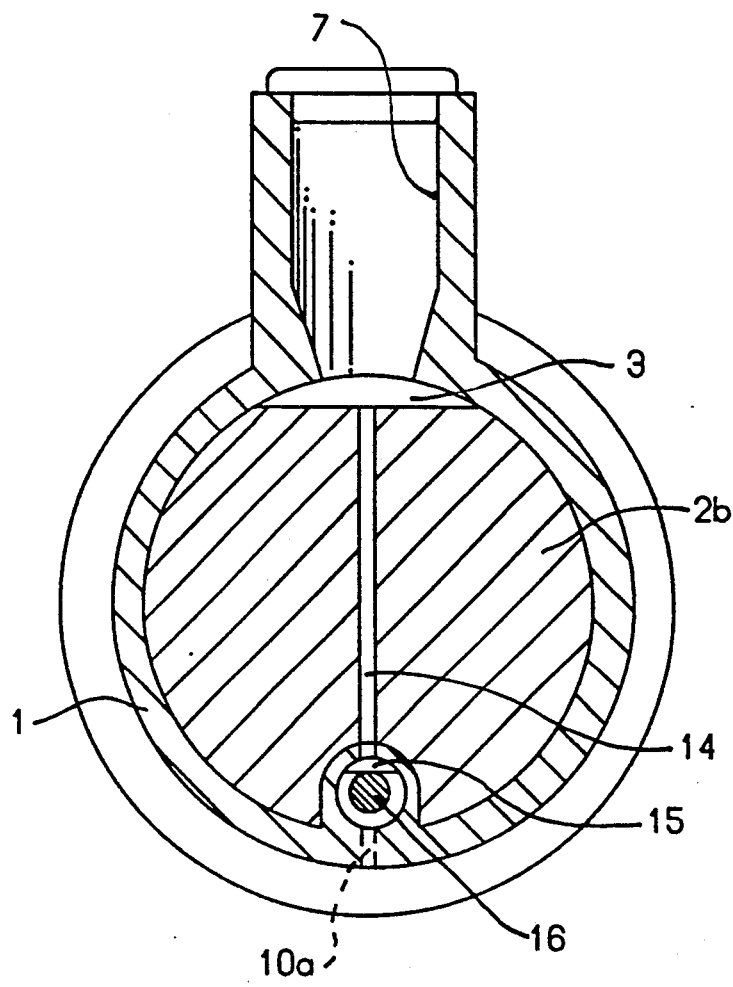
FIG. 5 is a section along V—V of FIG. 4.

FIGS. 4 and 5 show an additional security in the form of a valve 16. It can also be in the conventional form of a sleeve or insert along the rod 2b. Driven by the piston means with a clearance between two abutments 16a and 16b, its bearing surface 17 shuts the suction channel 14 during most of the advance travel corresponding to the aspiration phase to prevent any delivery when its outlet is cleared by the cavity 3. It only opens the passage 14 at the end of its movement toward the user's mouth when the piston head 2a strikes the abutment 16a. This opening of the passage 14 allows it to fulfil its function during the return travel as shown in FIG. 4 as the piston head 2a nears the end of its movement into its first position of the piston means. The engagement of the piston head 2a with the abutment 16a at the very end of the piston movement into its first position then recloses the passage 14.

Finally, the valve 16 also has a bearing surface 18. The valve thus serves as a distributor linking the chamber 10 by the orifice 10a to the open air during the advance movement of the piston toward the user's mouth.

What is claimed is:

1. An inhaler for powder products comprising:
   a) a housing having opposite ends, a charging section and at least one air chamber, one end of the housing defining a mouthpiece for insertion into a user's mouth, said mouthpiece having an internal volume and opening to the outside of the housing;
   b) piston means slideably mounted in said air chamber for movement between first and second positions toward and away from said one end; said first position being spaced farther from said one end than said second position, said piston means being mounted for said movement from said first position toward the one end of the housing when under an inhaling action by the user with the mouthpiece in the user's mouth;
   c) at least one connecting orifice connecting the internal volume of said mouthpiece with said chamber;
   d) elastic means for moving the piston means from said second position to said first position when the piston means is no longer under the inhaling action of the user;
   e) a charge cavity disposed in said piston means, said cavity having a predetermined volume for receiving a charge of powder;
   f) a powder reserve chamber in said charging section of said housing, said reserve chamber having a wall thereof defined by said piston means and being aligned with and communicating with said charge cavity when said piston means is in said first position to supply a charge of powder to said cavity; and
   g) a dispensing passage in said housing aligned with and in communication at one end thereof with said cavity and at another end with the internal volume of said mouthpiece when said piston means is in said second position whereby upon inhalation by the user, the piston means moves from said first position to said second position and the charge in said cavity is dispensed from said cavity into the internal volume of said mouthpiece to be inhaled by the user.

2. An inhaler according to claim 1 wherein:
a) said housing further include an air inlet vent connecting said charge cavity to the exterior of said housing when said piston means is in said second position.

3. An inhaler according to claim 2 wherein:
a) said dispensing passage is disposed immediately above and adjacent the connecting orifice where said orifice connects to the internal volume of said mouthpiece.

4. An inhaler according to claim 2 wherein:
a) said piston means defines one wall of a further chamber in said housing, the other end of which is vented to the mouthpiece.

5. An inhaler according to claim 2 wherein:
a) the piston means defines one wall of said air chamber in the other end of said housing, said air chamber being located between said piston means and the charging section of said housing.

6. An inhaler according to claim 2 wherein:
a) the piston means defines one wall of a further air chamber in said housing; and
b) said housing further includes a channel, one end of which is aligned with and in communication with said further air chamber and the other end of which communicates with said charge cavity as said piston reaches said first position whereby the movement of said piston means toward said first position creates a suction effect through said channel to draw a charge of powder into said cavity from said reserve chamber.

7. An inhaler according to claim 6, further including:
a) a valve mounted in communication with said connecting orifice for closing said connecting orifice.

8. An inhaler according to claim 7 wherein:
a) said connecting orifice is elongated and said valve is slideably mounted in said orifice and connected at one end to said piston means for movement therewith to close said channel from communication with said further chamber as said piston reaches said first position and while said piston moves toward said second position and to open said channel when said piston is in said second position and while said piston moves toward said first position.

9. An inhaler according to claim 8 wherein:
a) said housing further includes an air chamber vent connecting said connecting orifice to ambient atmosphere; and
b) said valve is positioned by said piston to open said air chamber vent when said piston is in said first position and while said piston moves toward said second position and to close said air chamber vent when said piston is in said second position and while said piston moves toward said first position.

* * * * *